US008993956B2

(12) United States Patent
Engelhardt et al.

(10) Patent No.: US 8,993,956 B2
(45) Date of Patent: *Mar. 31, 2015

(54) METHOD FOR CALIBRATING A SENSOR SYSTEM

(75) Inventors: Franz Engelhardt, Starnberg (DE); Norbert Holl, Germering (DE); Franz Nömmer, Dorfen (DE)

(73) Assignee: Giesecke & Devrient GmbH, Munich (DE)

( * ) Notice: Subject to any disclaimer, the term of this patent is extended or adjusted under 35 U.S.C. 154(b) by 1231 days.

This patent is subject to a terminal disclaimer.

(21) Appl. No.: 12/673,624

(22) PCT Filed: Aug. 14, 2008

(86) PCT No.: PCT/EP2008/006713
§ 371 (c)(1),
(2), (4) Date: Feb. 16, 2010

(87) PCT Pub. No.: WO2009/021746
PCT Pub. Date: Feb. 19, 2009

(65) Prior Publication Data
US 2011/0127414 A1 Jun. 2, 2011

(30) Foreign Application Priority Data
Aug. 16, 2007 (DE) .................. 10 2007 038 752

(51) Int. Cl.
*G01D 18/00* (2006.01)
*G07D 7/12* (2006.01)
*G01N 21/27* (2006.01)

(52) U.S. Cl.
CPC ................ *G07D 7/12* (2013.01); *G01N 21/278* (2013.01)
USPC ...................................... 250/252.1

(58) Field of Classification Search
USPC .......................... 250/252.1; 235/454; 356/306
See application file for complete search history.

(56) References Cited

U.S. PATENT DOCUMENTS 4,566,798 A   1/1986   Haas
4,587,434 A   5/1986   Roes et al.
(Continued)

FOREIGN PATENT DOCUMENTS

DE   102004021448 A1   11/2005
DE   WO2005106431     * 11/2005
WO   2006025846 A1    3/2006

OTHER PUBLICATIONS

International Search Report in PCT/EP2008/006713, Jan. 7, 2009.
(Continued)

*Primary Examiner* — David J Makiya
*Assistant Examiner* — Taeho Jo
(74) *Attorney, Agent, or Firm* — Workman Nydegger

(57) ABSTRACT

A method for the calibration of a sensor system is provided, the method including use of two calibration media. A high-quality first calibration medium, having a standardized reference independent of the sensor system to be calibrated, is used for a first calibration step in which the sensor system is calibrated and adjusted. A second calibration step immediately follows using a second calibration medium, having a non-standardized reference and being a component of the sensor system, to generate and store measuring signals of the second calibration medium with at least one sensor of the sensor system. Upon subsequent calibrations of the sensor system the second calibration medium is used exclusively so as to generate measuring signals of the second calibration medium with the sensor. If the measuring signals generated in the subsequent calibrations deviate from the stored measuring signals of the second calibration step, an adjustment of the sensor is effected.

10 Claims, 2 Drawing Sheets

(56) References Cited

U.S. PATENT DOCUMENTS

| | | | |
|---|---|---|---|
| 6,101,266 A * | 8/2000 | Laskowski et al. | 382/135 |
| 2001/0008275 A1 * | 7/2001 | Yanagiuchi | 250/559.4 |
| 2002/0179710 A1 * | 12/2002 | Gu et al. | 235/454 |
| 2005/0052648 A1 * | 3/2005 | Frick et al. | 356/328 |
| 2007/0181794 A1 | 8/2007 | Walsh et al. | |
| 2007/0236692 A1 * | 10/2007 | Schebesta et al. | 356/306 |
| 2011/0031386 A1 * | 2/2011 | Pradel | 250/252.1 |

OTHER PUBLICATIONS

Search Report of German Patent and Trademark Office regarding German Patent Application No. 10 2007 038 752.2, Aug. 27, 2008.

* cited by examiner

METHOD FOR CALIBRATING A SENSOR SYSTEM

The invention relates to a method for the calibration of a sensor system.

In order to ensure a correct function of sensors, sensors usually are calibrated. For the calibration of sensors there are used calibration media which have certain, predetermined properties. By means of these known properties it is possible to calibrate the sensors, because the known properties of the calibration media have to yield certain, expected measuring signals of the sensors. Thus it is possible to recognize deviations of the sensors, which are caused by e.g. manufacturing, ageing, soiling etc, and to take these into account in measurements. For this purpose, in a calibration mode it is ascertained whether the measuring signals of the sensors deviate from the measuring signals expected due to the calibration medium. The size of the ascertained deviations determines the adjustments of the sensor required for a correction of the deviations. For this purpose for example correction factors can be determined which are applied to the measuring signals of the sensors in subsequent measurements in the operating mode in order to compensate for the deviations. Likewise, the intensity of an excitation source, for example an illumination, can be changed upon the correction until the measuring signals of the sensor have the expected values. The changed intensity of the excitation source is maintained and subsequently used for measurements with the sensor, thereby compensating for the occurred deviations.

Special difficulties will arise, if great demands are made on the calibration of sensors, because by means of the sensors there are carried out sensible measurements, e.g. the recognition of documents of value, in the following referred to as bank notes, whose type (currency, denomination), authenticity, state (soiling, damage) etc is to be ascertained. Such cases require a very precise calibration of the sensors, since misjudgments due to wrong measuring signals of the sensors must be absolutely avoided. In this connection, the use of high-quality calibration media having standardized references, so-called measuring standards, has turned out to be problematic for various reasons.

From WO 2006/025846 A1 there is known a self-calibrating optical system which uses a high-quality calibration medium having a standardized white reference which is integrated in a sensor housing of the optical system. The calibration medium having the standardized white reference is pivoted into the optical path of the sensor during the calibration mode by means of a mechanism within the sensor housing. Due to the defined optical properties of the standardized white reference a self-calibration of the sensor is possible at any time. In the operating mode the calibration medium is pivoted out of the optical path of the sensor by means of the mechanism, in order to permit measurements of e.g. pharmaceutical products.

The self-calibrating optical system known from WO 2006/025846 A1, however, has the disadvantage, that a high-quality calibration medium having a standardized white reference has to be used so as to permit the desired self-calibration at any time. The use of the standardized white reference on the one hand has the disadvantage that such a standardized white reference has to be employed in each optical system to be calibrated, but such standardized references for the calibration are expensive. This results from the necessity to exactly measure the standardized references, since for the self-calibration it has to be ensured that the references exactly have the desired properties. On the other hand, despite the relatively protected accommodation of the standardized reference it may come to changes of the standardized reference e.g. due to ageing. In this case a reliable self-calibration of the sensor is no longer possible.

Furthermore, due to the accommodation of the calibration media having the standardized white reference within the sensor housing and the pivoting into the optical path of the sensor to be calibrated within the sensor housing there is always given a deviation from the actual measuring place of the sensor which is located outside the sensor housing. This problem is further aggravated, when the sensors or an associated illumination are to detect larger line-shaped or areal regions, so that they are built up, for example, as a line camera. Such sensors have a multiplicity of elements which are arranged side by side so as to form e.g. the line-shaped sensor or its illumination with a required length. Normally, such sensors or illuminations additionally have optical imaging systems. In such cases on the one hand it is desirable to perform a calibration for all the elements forming the sensor, on the other hand upon the known calibration there occurs blur, because the calibration medium does not lie in the focus area of the sensor within which the measurement of measuring objects, e.g. bank notes, is effected in the operating mode.

Starting out from this prior art, the invention is based on the object to provide a method for the calibration of a sensor system, which with decreased effort permits a precise and long-time stable calibration.

The solution to this problem appears from the features of claim 1. Developments are subject matter of the subclaims.

The invention starts out from a method for the calibration of a sensor system, having an operating mode, for the testing of measuring objects, in particular bank notes, and a calibration mode, for the calibration of the sensor system, in which in a first calibration step a first calibration medium independent of the sensor system, having a standardized reference, is brought into a focus area of the sensor system and covers the entire detection area of the sensor system, where the particular measuring object to be tested is located during the operating mode, wherein an excitation source of the sensor system excites the first calibration medium with an excitation signal, and a signal generated by the standardized reference of the first calibration medium due to the excitation signal is detected by at least one sensor of the sensor system and a measuring signal is generated, and wherein an adjustment of the sensor system is effected due to the measuring signal, and in a second calibration step which is performed immediately after the first calibration step, a second calibration medium having a non-standardized reference, and being a component of the sensor system, is brought into the optical path of the sensor system at a place which is shifted by a distance in relation to the focus area of the sensor system, and covers the entire detection area of the sensor system, wherein the excitation source of the sensor system excites the second calibration medium with the excitation signal, and a signal generated by the reference of the second calibration medium due to the excitation signal is detected by the sensor and a measuring signal is generated, and wherein the measuring signal of the second calibration step is stored, and in which further in the calibration mode the second calibration medium is again brought into the optical path of the sensor system at the place which is shifted by the distance in relation to the focus area of the sensor system, and covers the entire detection area of the sensor system, wherein the excitation source of the sensor system excites the second calibration medium with the excitation signal, and a signal generated by the reference of the second calibration medium due to the excitation signal is detected by the sensor and a measuring signal is generated, and wherein the measuring signal of the calibration mode is compared with the stored measuring signal of the second calibration step, and an adjustment of the sensor system is effected if the measuring signal of the calibration mode deviates from the stored measuring signal of the second calibration step.

The advantage of the method according to the invention is that only one high-quality calibration medium having a standardized reference has to be used so as to permit the desired calibration. This high-quality calibration medium has to be used only once, e.g. upon the manufacturing or repair of the sensor system to be calibrated. Since this high-quality calibration medium can be used for all sensor systems, it is additionally achieved that all sensor systems of a type are equally calibrated and thus provide comparable measuring signals for a certain measuring object.

For the calibration of the sensor system in the normal operation there can be used a cost-efficient calibration medium having a non-standardized reference. This, moreover, has the second advantage that the high-quality calibration medium having the standardized reference is not subjected to any harmful environmental influences during the operation of the sensor system, and changes of the cost-efficient calibration medium, having the non-standardized reference, are taken into account upon calibrating during the operation. This allows a long-time stable calibration of the sensor system. Additionally, in the method according to the invention deviations of the calibration medium from the actual measuring place of the sensor system are taken into account, which permits a substantially more precise calibration of the sensor system which, moreover, comprises the entire detection area of the sensor system.

Further embodiments and advantages of the invention are explained in the following with reference to the Figures and their description.

FIG. 1 shows a basic embodiment of a sensor system having calibration media upon performing a first calibration step.

FIG. 1 shows a basic embodiment of a sensor system having calibration media upon performing a first calibration step. FIG. 1a shows a section perpendicular to the longitudinal axis of the sensor system, while FIG. 1b represents a section parallel to the longitudinal axis of the sensor system, in a viewing direction A-A indicated in FIG. 1a.

Figure 1A:
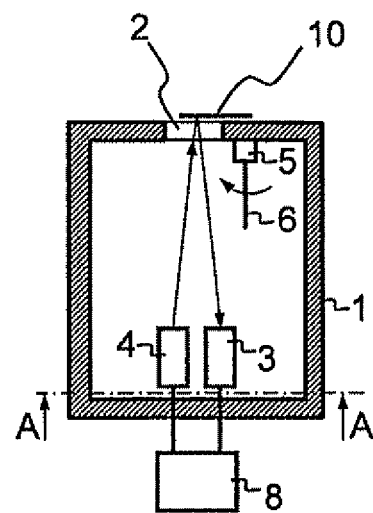

The sensor system comprises a sensor housing 1 which includes at least a sensor 3 and an excitation source 4. In the shown example the sensor 3 is a line camera which is formed by a number of detectors arranged side by side, e.g. photodiodes or by a CCD element. Likewise, two or more line cameras can be arranged in parallel side by side. The excitation source 4 is an illumination also built up in a line, which may consist of e.g. a number of elements arranged side by side such as light emitting diodes. The illumination 4 can emit for example white light, but it is also possible that illumination 4 emits light with certain spectral properties, e.g. infrared, red, green, blue, ultraviolet light etc. In the sensor housing 1 there is provided a window 2 which is transparent to the light of the illumination 4 and the light reflected back to the sensor 3. The sensor housing 1 can be formed in a dustproof manner so as to prevent a soiling of the sensor 3 or of the illumination 4. The sensor 3 and the illumination 4 are connected with a control device 8 which controls the sensor 3 and the illumination 4 and evaluates the signals of the sensor 3. The control device 8 may be formed for example by a microprocessor or a digital signal processor which may be provided with a volatile main memory and a nonvolatile memory for storing software and parameters required for the operation.

During the first calibration step shown in FIG. 1a a first calibration medium 10 is brought into the detection area of the sensor system. This can be effected for example by an operator, but it is also possible that the first calibration medium 10 is brought in by a transport system, which e.g. is component of a bank note processing machine in which the sensor system is mounted and used for testing bank notes. The first calibration medium 10 here is positioned such that it is located in the focus area of the sensor system, i.e. at a place where are also located the measuring objects to be examined during an operating mode, e.g. bank notes in the bank note processing machine. The first calibration medium 10 here is dimensioned such that it covers the entire detection area of the sensor system. That is, it has in particular a length which corresponds to a length of the sensor 3, such as shown e.g. in FIG. 1b, or to the length of its optical detection area. Advantageously, the first calibration medium 10 is designed so large that it covers the entire window 2. Thus preventing that the calibration by means of the first calibration medium 10 is influenced by external interfering signals. The first calibration medium 10 has a high-quality, standardized reference, in particular a standardized white reference. For example, for the standardized white reference Spectralon® can be used.

Controlled by the control device 8, in the first calibration step the first calibration medium 10 is illuminated with the illumination 4 and the light reflected by the first calibration medium 10 is detected by the sensor 3. The measuring signals of the sensor 3, for example for the intensity of the light reflected by the first calibration medium 10, are analyzed by the control device 8. Starting out from the first calibration medium 10 used having the standardized white reference and its thus exactly defined properties, an adjustment of the sensor system can be effected, when the intensities measured by the sensor 3 do not correspond to the intensities expected due to the known properties of the first calibration medium 10 used. Since the first calibration medium 10 extends over the entire sensor 3, for all detectors of the sensor 3 there are generated measuring signals which permit the calibration of the respective detectors. For adjusting the sensor system for example correction factors can be calculated which compensate for deviations present upon the calibration of the sensor system with the first calibration medium 10. The correction factors are stored in the nonvolatile memory of the control unit 8 and used in later measurements for generating the measuring signals. It can also be provided that the intensity of the illumination 4 or of its individual elements is changed by the control device 8, until the deviations present in the measurement are compensated for. In so doing, the determined parameters for the illumination 4 are also stored in the nonvolatile memory of the control device 8 for later measurements. Likewise, it is possible to provide both correction factors for the measuring signals and changed intensities of the illumination 4, thus permitting a compensation for present deviations. At the end of the first calibration step, in addition, the measuring signals of the sensor 4 or of the individual detectors can be stored for later comparisons.

Advantageously, it is provided that the first calibration step is performed only once, e.g. upon the manufacturing or after a repair of the sensor system, so that only for the first calibration step a calibration medium having a standardized white reference has to be provided.

Immediately after the first calibration step, a second calibration step is performed with the sensor system adjusted in the first calibration step. For this, within the sensor housing 1 a second calibration medium 6 is provided, which has a reference with, likewise, defined properties, for example a white reference. But, as it will be explained in the following, one can do without the use of a standardized and thus expensive reference within the sensor system as a component of the second calibration medium 6.

For the second calibration step, as indicated in FIG. 1*a* by an arrow, the second calibration medium 6 is brought into the optical path of the sensor 3. This can be effected for example, as shown, by rotating or swiveling. But the second calibration medium 6 can also be brought into the optical path of the sensor 3 in another way, e.g. by pivoting, pushing etc.

Figure 1B:
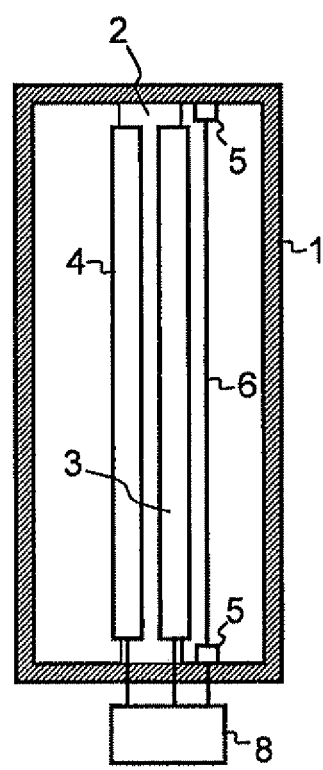
Figure 2A:
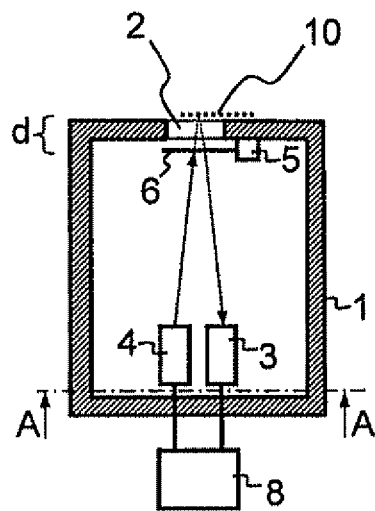
FIG. 2 shows the sensor system according to FIG. 1 upon performing a second calibration step or in a calibration mode.
Figure 2B:
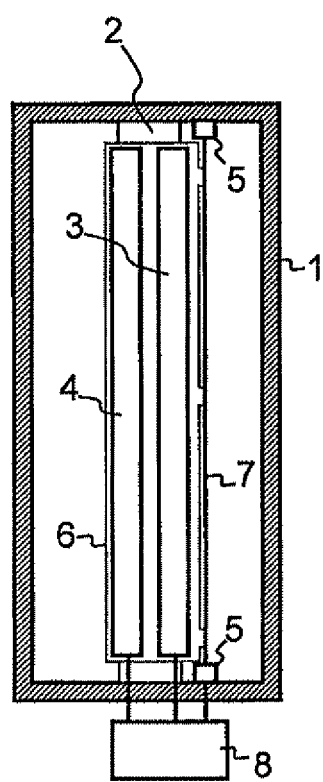

As apparent from FIGS. 1*b* and 2*b*, the second calibration medium 6 is fastened at an axle 7, which is provided with a drive 5 which is controlled by the control device 8. The second calibration medium 6 is brought into the optical path, controlled by the control device 8, by means of drive 5 and axle 7. As apparent from FIG. 2*a*, the second calibration medium 6 is positioned directly in front of the window 2 within the sensor housing 1. The second calibration medium 6 also extends over the entire detection area of the sensor 3 (FIG. 2*b*), which permits a calibration of all detectors of the sensor 3. Advantageously, the second calibration medium 6 is designed so large that it covers the entire window 2. Thus preventing that the calibration by means of the second calibration medium 6 is influenced by external interfering signals.

The second calibration medium 6 has a white reference with properties which in principle correspond to the properties of the standardized white reference of the first calibration medium 10. The white reference of the second calibration medium 6, however, in contrast to the white reference of the first calibration medium 10 is non-standardized. Likewise, it is possible that the second calibration medium 6 is provided with a reference which has properties which are at least similar to the properties of the reference of the first calibration medium 10. In the case of the white reference used for the reference of the first calibration medium 10, for example for the second calibration medium 6 a reference can be used which is white or relatively bright. Ideally, the properties of the reference of the second calibration medium 6 should have a good ageing stability. As a reference for the second calibration medium 6 for example bank note paper can be used.

In the second calibration step an illumination of the second calibration medium 6 or its white reference is effected by the illumination 4. If, as described above for the first calibration step, the intensity of the illumination 4 was changed for the adjustment, the illumination is operated with this changed intensity. The light reflected by the second calibration medium 6 is detected by the sensor 3 or the individual detectors and converted into corresponding measuring signals, for example for the intensity of light reflected from the second calibration medium 6. While in the above-described first calibration step there were determined and stored correction factors, these are used upon the generation of the measuring signals by the control device 8. The measuring signals of the sensor 3 or of the individual detectors for the second calibration medium 6 are stored by the control device 8 in its nonvolatile memory at the end of the second calibration step.

The measuring signals of the second calibration step normally will differ from the measuring signals of the first calibration step, because these measuring signals on the one hand express that not the first calibration medium 10 having the standardized white reference is used. On the other hand, it becomes noticeable that the second calibration medium 6 for the measurement is not arranged outside the sensor housing 1 in the focus area of the sensor 3 like the first calibration medium 10 as indicated by dashed lines in FIG. 3, but moved by a distance d into the sensor housing 1 and thus is located by the distance d outside the focus area of the sensor system or of the sensor 3 and/or of the illumination 4. Since the second calibration step is performed immediately after the first calibration step, the measuring signals of the second calibration step represent a basis for later calibrations and adjustments of the sensor system or of the sensor 3 and/or of the illumination 4 during the normal operation. The basically disadvantageous deviations of the non-standardized properties of the second calibration medium 6 as well as the basically disadvantageous moving of the second calibration medium 6 by the distance d out from the focus area of the sensor 3 or of the illumination 4 thus are automatically included, and so they are also automatically taken into account upon later calibrations with the second calibration medium 6 or its reference and cannot negatively affect the calibration procedure. Moreover, e.g. changes of the second calibration medium 6 due to ageing thus cannot falsely affect later calibration processes, since these always cause changed measuring signals which are compensated for upon the calibration.

For the operating mode, the second reference medium 6 is removed from the optical path of the sensor 3 or of the illumination 4 under the control of the control device 8 by the drive 5. During the operating mode, then there are brought in measuring objects, e.g. bank notes, at the place for the first reference medium 10 shown in FIG. 1*a*. For this purpose, for example a transport system of a bank note processing machine can be used, in which the sensor system is used for testing bank notes. Upon the evaluation of the measuring signals of the sensor 3 by the control device 8, for testing bank notes in the operating mode the above-described correction factors and/or the changed intensity of the illumination 4 are used.

After predetermined periods of use of the sensor system or upon switching on the sensor system or the bank note processing machine having the sensor system it can be provided that a re-calibration and re-adjustment of the sensor system or of the sensor 3 and/or of the illumination is performed in a calibration mode. For this purpose, like in the above-described second calibration step, the second calibration medium 6 is brought into the optical path of the sensor 3 and/or of the illumination 4 by the drive 5. The measuring signals of the sensor 3 or of the individual detectors ascertained upon the re-calibration are compared with the measuring signals of the second calibration step stored in the nonvolatile memory of the control device 8. If deviations occur, the sensor system, i.e. the sensor 3 and/or the illumination 4, is adjusted in the way described above for the first calibration step. For this purpose, correction factors for correcting the deviations of the measuring signals are ascertained and/or the intensity of the illumination 4 or of its individual elements is changed. The correction factors or the change of the intensity of the illumination 4 are stored in the nonvolatile memory of the control device 8 and are subsequently used in the operating mode, for which the second calibration medium 6, under the control of the control device 8 by the drive 5, again is removed from the optical path of the sensor 3.

The deviations ascertained upon the re-calibration between the measuring signals ascertained upon the calibration and the measuring signals of the second calibration step stored in the nonvolatile memory of the control device 8, moreover, allow a statement about certain drift phenomena of the sensor system, i.e. changes of sensor 3, illumination 4, second calibration medium 6 etc due to ageing, soiling, etc.

In the above-described embodiment there is shown a sensor 3 measuring in reflection with associated illumination 4. But it is obvious that a sensor measuring in transmitted light can also be calibrated with an illumination located opposite the sensor outside the sensor housing 1. For this, the calibration media 6, 10 have to be chosen accordingly, in particular these have to be transparent to at least a part of the light of the illumination 4. It is obvious that, besides the described optical sensors, other sensors can be calibrated with the proposed method, when calibration media 6, with appropriate sensor-specific properties are chosen.

In the above description there was explained by way of example, that the adjustment of the sensor system due to the deviations ascertained upon the calibration can be effected by means of correction factors and/or a change of the intensity of the excitation source. The adjustment of the sensor system, i.e. the correction of the ascertained deviations, however, can also be achieved in other ways. For example, the amplification of amplifiers can be changed, with which the measuring signals coming from the sensor or the individual detectors are amplified for the further processing.

The invention claimed is:

1. A method for the calibration of a sensor system having an operating mode for the testing of measuring objects and a calibration mode for the calibration of the sensor system, the method comprising:
   a first calibration step, in which a first calibration medium independent of the sensor system, having a standardized reference, is brought into a focus area of the sensor system so that the first calibration medium covers the entire detection area of the sensor system where the particular measuring object to be tested is located during the operating mode; an excitation source of the sensor system excites the first calibration medium with an excitation signal to generate a signal is by the standardized reference of the first calibration medium due to the excitation signal being detected by at least one sensor of the sensor system to generate a measuring signal; and an adjustment of the sensor system is effected using the measuring signal;
   a second calibration step which is performed immediately after the first calibration step, wherein a second calibration medium, having a non-standardized reference, and being a component of the sensor system, is brought into the optical path of the sensor system at a place which is shifted by a distance (d) in relation to the focus area of the sensor system, so that the second calibration medium covers the entire detection area of the sensor system; the excitation source of the sensor system excites the second calibration medium with the excitation signal to generate a signal by the reference of the second calibration medium due to the excitation signal being detected by the sensor to generate a measuring signal, wherein correction factors obtained from the first calibration step are used in the second calibration step upon the generation of the measuring signal of the second calibration step;
   the measuring signal of the second calibration step is stored;
   in the calibration mode, the second calibration medium is again brought into the optical path of the sensor system at the place which is shifted by the distance (d) in relation to the focus area of the sensor system, and covers the entire detection area of the sensor system;
   the excitation source of the sensor system excites the second calibration medium with the excitation signal to generate a signal by the reference of the second calibration medium due to the excitation signal being detected by the sensor to generate a measuring signal;
   the measuring signal of the calibration mode is compared with the stored measuring signal of the second calibration step; and
   an adjustment of the sensor system is effected if the measuring signal of the calibration mode deviates from the stored measuring signal of the second calibration step.

2. The method according to claim 1, wherein the reference of the second calibration medium and the reference of the first calibration medium are selected so they have comparable properties.

3. The method according to claim 1, wherein the calibration and adjustment of the sensor system are effected for a multiplicity of detectors forming the sensor and for each detector a measuring signal is generated and stored.

4. The method according to claim 1, wherein for adjusting the sensor system correction factors are determined, with which the measuring signals of the sensor are corrected.

5. The method according to claim 1, wherein for adjusting the sensor system an intensity of the excitation signal of the excitation source is changed.

6. The method according to claim 1, wherein the excitation source generates an optical excitation signal and the sensor detects an optical signal.

7. The method according to claim 6, wherein for the first calibration medium a standardized white reference is used and for the second calibration medium a non-standardized white reference is used.

8. The method according to claim 1, wherein the measuring objects are bank notes.

9. The method according to claim 1, wherein for the first calibration medium only a standardized white reference is used and for the second calibration medium only a non-standardized white reference is used.

10. The method according to claim 1, wherein the non-standardized reference is bank-note paper.

* * * * *